United States Patent [19]

Knott et al.

[11] 4,167,583

[45] Sep. 11, 1979

[54] MICROBIAL COMPOSITION AND FORMULATIONS

[75] Inventors: Therese Knott, Wuppertal; Karlheinz Adams, Cologne; Erich Klauke, Odenthal-Hahnenberg, all of Fed. Rep. of Germany

[73] Assignee: Bayer Aktiengesellschaft, Fed. Rep. of Germany

[21] Appl. No.: 859,698

[22] Filed: Dec. 12, 1977

Related U.S. Application Data

[63] Continuation-in-part of Ser. No. 605,723, Aug. 18, 1975, abandoned, which is a continuation-in-part of Ser. No. 485,299, Jul. 2, 1974, abandoned.

[30] Foreign Application Priority Data

Jul. 3, 1973 [DE] Fed. Rep. of Germany ....... 2333849

[51] Int. Cl.$^2$ .................... A61K 31/045; A61K 31/14
[52] U.S. Cl. .................................... 424/343; 424/329
[58] Field of Search ................................ 424/343, 329

[56] References Cited

U.S. PATENT DOCUMENTS 2,945,782  7/1960  Schraufstatter et al. ............ 424/343

OTHER PUBLICATIONS

Chemical Abstracts, 41:495e (1947).
Chemical Abstracts, 61:2916b (1964).

*Primary Examiner*—Jerome D. Goldberg
*Attorney, Agent, or Firm*—Jacobs & Jacobs

[57] ABSTRACT

A superior antimicrobial composition consists of an aqueous solution of 65 to 75 parts by weight of at least one propanol and 0.1 to 1 part by weight of a dichlorobenzyl alcohol. The solution can be utilized in the preparation of microbicidal formulations for topical application.

16 Claims, No Drawings

MICROBIAL COMPOSITION AND FORMULATIONS

CROSS-REFERENCE

This is a continuation-in-part of Ser. No. 605,723 filed Aug. 18, 1975 which in turn is a continuation-in-part of Ser. No. 485,299 filed July 2, 1974, both now abandoned.

DETAILED DESCRIPTION

This invention relates to a new microbicidal composition demonstrating a synergistic effect and comprising known alkanols and benzyl alcohols.

Aqueous solutions of primary alkanols are known to exhibit microbicidal activity. In practice, only ethanol and propanol have acquired general acceptance and their high volatility when exposed to the atmosphere results in rapid dissipation and thus a very short duration of effectiveness.

2,4-Dichlorobenzyl alcohol is also a known microbicide but, in practice, its action is not entirely satisfactory, largely because of solubility problems. U.S. Pat. No. 2,948,782, for example, describes an aqueous solution of 15% 3,4-dichlorobenzyl alcohol and 20% isopropanol requiring however an anionic surfactant to be present in relatively large amounts (about 16%) in order to achieve satisfactory disinfecting concentrations of active ingredient. A mixture of dichlorobenzyl alcohol, isopropanol and butyl glycol is also known, but this mixture requires prior dilution to form aqueous solutions just prior to use thus necessitating facilities for immersion and rinsing.

This invention provides a new aqueous microbicidal composition which overcomes the disadvantages associated with known microbicidal preparations and to formulations utilizing this composition.

In addition, this invention also relates to a novel method of disinfecting the skin of humans and other animals by topically applying formulations containing this composition.

The following dichlorobenzyl alcohols are typical of those which can be employed: 2,3-dichlorobenzyl alcohol; 2,4-dichlorobenzyl alcohol; 3,4-dichlorobenzyl alcohol; and 2,6-dichlorobenzyl alcohol. The dichlorobenzyl alcohol can be present as individual, chemically discrete isomers or as mixtures, obtained through either blending or as the inherent product of chemical synthesis in which several isomers are formed. 3,4-Dichlorobenzyl alcohol is preferred.

The propanol can be either n-propanol or isopropanol or both. In addition therefore to containing one ingredient each of the propanol and dichlorobenzyl alcohol, the compositions can contain two propanols combined with two or more benzyl alcohols. One such preferred embodiment comprises a composition containing a mixture of n-propanol and isopropanol in combination with a mixture of two or more of the isomers 2,3-dichlorobenzyl alcohol, 2,4-dichlorobenzyl alcohol and/or 3,4-dichlorobenzyl alcohol.

The compositions afford a high intensity of initial anti-microbial activity, and possess a long-lasting action. They are well tolerated by humans and animals when administered topically. The compositions can be administered directly even in the absence of wash or rinse facilities, a particularly desirable characteristic since they can be used directly at the sick bed or at the site of an accident without the need for a subsequent rinsing with water or other diluent.

The instant compositions exhibit an anti-microbial effect which is greater than that attributable to the propanol and dichlorobenzyl alcohol ingredients individually. Thus, the activity of the composition is synergistic in effect and the degree of microbial activity is totally unexpected.

The microbicidal composition is characterized by the low proportion of dichlorobenzyl alcohol, namely from about 0.1 to about 1% by weight. As is evidenced by the teachings of U.S. Pat. No. 2,945,782, the art has attempted to prepare highly concentrated solutions; e.g. 15%, and overcome the low solubility of dichlorobenzyl alcohol through inclusion of an approximate equal amount of an anionic surfactant such as a paraffin sulfonate. Although these concentrated solutions also contain isopropanol in an amount of 20%, it appears this serves primarily as a solvent for the dichlorobenzyl alcohol since upon dilution at 1:50 prior to application its effective concentration is only 0.4%.

In contrast, the present composition contains a low level of dichlorobenzyl alcohol, as indicated above, and a high percentage, 65 to 75% by weight, of at least one propanol. Preferably, both propanols are used; e.g. a 3:4 mixture of n-propanol and isopropanol.

The significance of the parameters of this composition can be summarized as follows. It can be demonstrated by recognized assays that paraffin or alkylsulfonate itself has no significant antimicrobial activity, neither as a simple aqueous solution nor as an aqueous propanol solution. On the other hand the sulfonate can dramatically increase the activity of the dichlorobenzyl alcohol, possibly by altering the permeability of the microorganism. This enhancement in activity through the use of a sulfonate surfactant is in accordance with the teachings of U.S. Pat. No. 2,945,782. An increase in the propanol content in the prior art composition does not significantly alter this activity nor does a reduction in the amount of surfactant. The complete elimination of the surfactant however results in a significant decrease in activity, even though the surfactant itself has no activity. However with a decrease in the amount of 3,4-dichlorobenzyl alcohol and an increase in the amount of propanol to produce a ratio to dichlorobenzyl alcohol to propanol of approximately 1:70, a significant increase in activity results, and this without the presence of a surfactant.

The compositions are effective against a wide range of microbes including Gram negative and Gram positive bacterial and bacteria-like pathogens. They are particularly suitable for combatting common pathogenic causative organisms and, especially, intractable germs which are of concern in clinical practice and frequently combatted only with difficulty.

The instant composition can also be used for the disinfection of inanimate objects such as medical instruments and equipment and in the production, handling or storage of food or drink. They are suitable for use in both human and veterinary medicine, in general in the care of both healthy or sick humans or animals, namely, wherever the transfer of pathogens is to be prevented. Because of their outstanding toleration by skin they are however particularly suitable for use for disinfecting the hands for hygienic and surgical purposes.

The instant compositions are used in accordance with the generally customary methods as by immersion or by direct application. The compositions can be simply rubbed into the hands with gentle washing movements to effect disinfection.

After any excess has been allowed to drip off, the hands can be shaken until dry. The disinfectant action takes effect within a few seconds. To disinfect the remainder of the skin, the agent can be sprayed on and allowed to dry.

Since an immediate and major reduction in the permanent skin flora occurs, there is also no need to fear a significant increase in the microbes under rubber gloves in the case of surgery, given normal operation durations.

Examples of bacteria, bacteria-like organisms, and fungi against which the compositions of the invention are effective include Micrococcaceae, such as Staphylococci, as for example *S. aureus, S. epidermidis, S. aerogenes* and *Gaffkya tetragene;* Lactobacteriaceae, such as Streptococci, for example *Str. pyrogenes,* α- and β-haemolysing streptococci, non (γ-)-haemolysing streptococci, *Str. viridans, Str. faecalis* (enterococci), *Str. agalactiae, Str. lactis, Str. equi, Str. anaerobis* and *Diplococcus pneumoniae;* Neisseriaceaae, such as Neisseriae, as for example *N. gonorrhoeae, N. meningitidis, N. catarrhalis* and *N. flava;* Corynebacteriaceae, such as Corynebacteria, for example *C. diphtheriae, C. pyrogenes, C. diphtheroides, C. acnes, C. parvum, C. bovis, C. renale, C. ovis* and *C. murisepticum;* Listeria bacteria, for example *Listeria monocytogenes;* Erysipelothrix bacteria, for example *Erysipelothrix insidiosa;* Kurthia bacteria, for example *Kurthia zopfii;* Mycobacteriaceae, such as pathogens of mycobacterioses, as for example *M. tuberculosis, M. bovis, M. avium,* as well as the so-called atypical mycobacteria from Runyon groups I, II, III and IV; *M. leprae;* Enterobacteriaceae, such as Escherichia bacteria, as for example *E. coli;* Aerobacter bacteria, for example *A. aerogenes* and *A. cloacae;* Klebsiella bacteria, for example *K. pneumoniae* and *K. ozaenae;* Erwiniae, as for example Erwinia spec.; Serratia, for example *Serratia marcescens;* Proteae bacteria of the Proteus group, such as for example *Pr. vulgaris, Pr. morganii, Pr. rettgeri* and *Pr. mirabilis;* Providencia, as for example Providencia sp., Salmonelleae; Salmonella bacteria, for example *S. paratyphi* A and B, *S. typhi, S. enteritidis, S. cholera suis* and *S. typhimurium;* and Shigella bacteria, as for example *Sh. dysenteriae, Sh. ambigua, Sh. flexneri, Sh. boydii* and *Sh. sonnei;* Pseudomonadaceae, such as Pseudomonas bacteria, as for example *Ps. aeruginosa* and *Ps. pseudomallei;* and Aeromonas bacteria, as for example *A. liquefaciens* and *A. hydrophila;* Spirillaceae, such as Vibrio bacteria, for example *V. cholerae, V. proteus* and *V. fetus;* Spirillum bacteria, as for example *Spirillum minus;* Parvobacteriaceae or Brucellaceae, such as Pasteurella bacteria, as for example *Past. multocida, Past. pestis* (Yersinia), *Past. pseudotuberculosis* and *Past. tularensis;* Brucella bacteria, for example *Br. abortus, Br. melitensis* and *Br. suis;* Haemophilus bacteria, as for example *H. influenzae, H. ducreyi, H. suis, H. canis* and *H. aegypticus;* Bordetella bacteria, for example *B. pertussis* and *B. bronchiseptica;* and Morazella bacteria, for example *Morazella lacunata;* Bacterioidaceae, such as Bacteroides bacteria, as for example *B. fragilis* and *B. serpens;* Fusiforme bacteria, for example *Fusobacterium fusiforme;* Sphaerophorus bacteria, for example *Sph. necrophorus, Sph. necroticus* and *Sph. pyogenes;* Achromobacteriaceae, such as Flavobacterium, *Alcaligensis faecalis* and Achromobacter, as for example *Achromobacter anitratus;* Actinobacillosis bacteria, such as *Act. mallei* and *Act. lignieresii;* Bartonellae, for example *Bartonella bacilliformis;* Mimae, such as Mima bacteria, as for example *Mima polymorpha,* and Herellae bacteria, as for example *Herellea vaginocola;* Actinomycetaceae, such as Actinomycetes, for example *Act. israeli, Act. bovis* and *Act. baudettii;* Nocardiae, as for example *N. asteroides* and *N. brasiliensis (N. madura);* Bacillaceae, such as aerobic spore-formers, for example *B. anthracis, B. subtilis* and *B. cereus;* anaerobis spore-formers, such as Clostridia, as for example *Cl. perfringens, Cl. speticum, Cl. oedematiens, Cl. histolyticum, Cl. tetani* and *Cl. botulinum;* Spirchaetaceae, such as Borrelia bacteria, as for example *b. recurrentia* and *B. vincentii;* Treponema bacteria, for example *Tr. pallidum, Tr. pertinue* and *Tr. carateum;* Leptospira bacteria, as for example *L. interrogans, L. icterohaemorrhagiae, L. canicola, L. grippotyphosa, L. pomona, L. mitis* and *L. bovis;* Rickettsiales and other bacteria-like microorganisms, such as Rickettsiaceae, as for example *R. prowazeki, R. mooseri, R. rickettsi, R. sibirica, R. akari, R. orientalis, R. burneti* and *R. quintana;* Chlamydiaceae, as for example *Chl. psittaci, Chl. lymphogranulomatosis, Chl. trachomatis* and *Chl. oculogenitalis* and Mycoplasma such as *M. pneumoniae, M. hominis, M. suis pneumoniae, M. gallisepticum* and *M. hyorhinis.*

Examples of fungi include the causative organisms of candidamycoses, such as *C. albicans, C. parasilosis* and *C. tropicalis;* of cryptococcoses, as for example *Cryptococcus neoformans;* of mould diseases, such as *Asp. fumigatus, Asp. niger, Asp. flavus, Asp. nidulans, Pen. bertai, Pen. crustaceum* and *Pen. commune;* of dermatomycoses, such as Trichophyton, as for example *Tr. mentagrophytes, Tr. rubrum, Tr. schoenleinii, Tr. tonsurans, Tr. flavum, Tr. quinckeanum, Tr. verucosum* and *Tr. persicolor,* and Microsporon, for example *M. audonini, M. canis* and *M. gypseum* and Epidermophyton as for example *Epidermophyton floccosum;* of hystoplasmoses, as for example *Histoplasma capsulatum* and *Histoplasma duboisii;* of coccidiodomycoses, as for example *Coccidioides immitis;* and of blastomycoses, for example *Blastomyces brasiliensis* and *Blastomyces dermatitides.*

The microbicidal activity of the new compositions can be demonstrated by the following models utilizing *Staphylococcus aureus* and *Pseudomonas pyocyaneus.*

A culture was grown for 4 hours at 37° C. with rotating agitation in brain-heart broth. On the following day, 0.5 ml was transinoculated into about 7 ml of brain-heart broth. Incubation was performed for about 16 hours at 37° C. The resulting culture was diluted to $10^{-4}$ in NaCl-phosphate buffer (pH 7.2). The number of individual cells in this suspension was about $1 \times 10^5$ ($7.5 \times 10^4$ to $2 \times 10^5$) cells per ml. The diluted culture was maintained at a temperature of 35° C. in a waterbath.

Each test mixture was prepared in 10-fold strength with NaCl-phosphate buffer. At time "zero", 9 ml of microbial suspension ($10^{-4}$ cells) were mixed with 1.0 ml of test composition; one tube was used, per test strain and composition and per concentration, for all sampling times. A $10^{-4}$ cell suspension in 1.0 ml of NaCl buffer was used as control. After the indicated period of action, 1.0 ml of cell-preparation mixture ("concentrate") was withdrawn. Of this sample, half (0.5 ml) was immediately diluted 1:10 with NaCl buffer and 0.5 ml of this diluted mixture was poured, together with 10 ml of liquefied nutrient agar, into Petri dishes. The remaining half of the 1:10 dilution was used for the next 1:10 dilution (1:100), and the process repeated until the $10^{-4}$ to $10^{-5}$ stage was reached. The incubation was carried out at 37° C. for 48 hours and thereafter the colonies were counted, multiplied by 2 (to convert to 1.0 ml) and converted back to the concentrate, in accordance with the dilution stage, thus giving the number of surviving cells.

It was not necessary to add inactivating agents to the agar of NaCl buffer of the dilution series, since the preparation test concentrations selected lay in the threshold range and in any case went below the action threshold in the agar.

The concentrations used in the experiments are about 1/10 lower than in the microbicidal compositions according to this invention. These low concentrations are suitable for demonstrating the synergistic effect since at full composition the active ingredients in the compositions are too powerful and the germs are killed too rapidly to permit experimental observation. The increase in action can thus be demonstrated only by comparing the action of the individual components with mixtures thereof in limiting or minimal concentration ranges. The breadth of scatter in the experiment is predominantly attributable to the scale of the experiment, the requirements for sterility when carrying out the experiment, the equipment (e.g. pipettes) and slight errors in timing. This scatter appears, from numerous experiments in inoculation with the germs and counting the growth on the plates, to involve a factor of about 0.5–2 from the average value and value shown by experience. However, since the synergistic effect expresses itself in a reduction in the number of germs by up to five powers of 10, this degree of fluctuation can be neglected. In the case of the number of microbial cells determined, and the change in the number of cells, in %, calculated therefrom, the values were rounded up or down to 5 or 0.

The experimental results are listed in Tables 1 to 5.

In these experiments the dichlorobenzyl alcohol used was a mixture of the 3,4- and 2,4-isomers. The sumbols "+" and "−" indicate respectively an increase and a decrease in the number of cells.

Table IA

*Staphylococcus aureus*

| Test Comp. | Conc. g/100 g. | No. of cells/ml at 60 min. | % Change |
|---|---|---|---|
| Control | — | $1.5 \times 10^5$ | +50 |
| Isopropanol | 5 | $6 \times 10^4$ | −40 |
| 3:4 Propanol:isopropanyl | 5 | $3 \times 10^4$ | −70 |
| Dichlorobenzyl alcohol | 0.012 | $9 \times 10^4$ | −10 |
|  | 0.025 | $3.5 \times 10^4$ | −65 |
| Isopropanol Dichlorobenzyl Alcohol | 5 0.025 | $2 \times 10^3$ | −98 |
| 3:4 Propanol:Isopropanol Dichlorobenzyl alcohol | 5 0.012 | $6 \times 10^2$ | −98.5 |

Table IB

*Pseudomonas pyrocyaneus*

| Test Comp. | Conc. g/100 g | No. of Cells/ml at 60 min. | % Change |
|---|---|---|---|
| Control | — | $1.5 \times 10^5$ | 0 |
| Isopropanol | 5 | $9.5 \times 10^4$ | −35 |
| Dichlorobenzyl alcohol | 0.012 | $1.5 \times 10^5$ | 0 |
|  | 0.0125 | $5.0 \times 10^5$ | −65 |
| Isopropanol Dichlorobenzyl alcohol | 5 0.025 | <10 | −>99.9 |
| 3:4 Propanyl:Isopropanyl Dichlorobenzyl alcohol | 5 0.012 | <10 | −>99.9 |

To evaluate the rapidity with which the compositions act, a measurement of bacterial cell concentration was made at 10 minutes. Experiments were conducted with *S. aureus* at initial cell concentrations of $1.5 \times 10^5$ (Table IIA) and $7.5 \times 10^4$ (Table IIB):

Table IIA

*Staphylococcus aureus*
$1.5 \times 10^5$ cells/ml

| Test Comp. | Conc. g/100 g. | No. of cells/ml at 10 min. | % Change |
|---|---|---|---|
| Control | — | $9.5 \times 10^4$ | −35 |
| 3:4 Propanol:Isopropanol | 5 | $5.5 \times 10^5$ | −65 |
| Dichlorobenzyl alcohol | 0.05 | $5.5 \times 10^5$ | −65 |
| 3:4 Propanol:Isopropanol Dichlorobenzyl alcohol | 5 0.05 | $1.5 \times 10^2$ | −99.9 |

Table IIB

*Staphylococcus aureus*
$7.5 \times 10^4$ cells/ml

| Test Comp. | Conc. g/100 g. | No. of cells/ml at 10 min. | % Change |
|---|---|---|---|
| Control | — | $7.5 \times 10^4$ | 0 |
| 3:4 Propanol:Isopropanol | 5 | $6.5 \times 10^4$ | 0 |
| Dichlorobenzyl alcohol | 0.025 | $9 \times 10^4$ | 0 |
| 3:4 Propanol-Isopropanol Dichlorobenzyl alcohol | 5 0.025 | $2 \times 10^3$ | −97 |

The compositions of this invention are administered topically in liquid or semi-liquid dosage unit forms such as dilutions, suspensions, ointments, pastes, creams and gels. For this purpose, topical formulations can be prepared containing the microbicidal compositions together with various auxiliaries. These auxiliaries are often desirable to produce a superior cosmetic preparation such as by thickening or by providing a pleasant scent but do not significantly alter the microbicidal properties of the composition which is the preponderant component of the formulation; i.e. constituting 95% or more of the components of the formulation.

One group of auxiliaries are those which serve as protectants and as surface active agents, improving the wetting of the object or surface to be disinfected. Moreover these exhibit a "fat-restoring" effect on human or animal skin and improve the viscosity of the compositions. Such known auxiliaries include glycerol, polyethylene glycol, polypropylene glycol, urea, polyfinylpyrolidone, dextran, sorbitol and propylene glycol. Surface-active agents include lecithin, ampholytic soaps, sodium laurylsarcosinate, sodium ricinoleate, sodium salts of highly sulphated fatty acids, partial glyceride mixtures of natural saturated vegetable fatty acids of medium chain length, ammonium aluryl-ether-sulphate, sulphate, sulphosuccinates of long-chain alkylolamides, sodium dodecylbenzene-sulphonate, sodium lauryl-ether-sulphate, sodium lauryl-sulphate and sulphosuccinic acid half-esters of lauryl polyglycol ethers. Organic phosphorus compounds in which compounds of the fatty series ($C_{12}$ to $C_{14}$ preferably) are bonded directly or via an ethylene oxide bridge to orthophosphoric acid such as the ester derivative thereof can also be present. Preferred among these additives are the tertiary ester of orthophosphoric acid and lauryl tetraglycol ether.

The compositions can of course include commercially available scents so as to enhance their appeal.

A second group of auxiliaries are those by which the pH of the compositions can be adjusted, to a value which is suitable for contact with the skin, namely, a pH value of from about 6 1 to 6.5. Of these buffers, one found to be particularly suitable is an aqueous mixture of lactic acid and sodium lactate. The water used in preparing said buffer should be either distilled or demineralized so as to be dermatologically acceptable.

A third type of auxiliary includes antibacterial quaternary ammonium salts. This class of cationic agents, of which benzalkonium chloride is preferred but which includes other quaternaries such as centrimonium chloride, cetalkonium chloride, imidecyl iodine and the like, are often useful to extend the activity of the composition against certain microorganisms which are particularly sensitive to such cationic agents, such as some strains of Mycobacterium and Mycoplasma. They are unlike the prior art alkyl sulfonate anionic surfactants in several regards, notably the low concentration in which they are present (less than 2), the absence of any solubilizing effect on the dichlorobenzyl alcohols and their inherent antimicrobial properties.

A preferred embodiment of this invention comprises a composition which on a 100 parts by weight basis contains 65 to 75 parts by weight of a propanol, and most preferably 70 parts by weight of 3:4 n-propanol-:isopropanol, and 0.2 to 0.5 parts by weight of a dichlorobenzyl alcohol, and most preferably 0.3 parts by weight of a 3,4-dichlorobenzyl alcohol.

A preferred topical antimicrobial formulation includes as its preponderant component an aqueous solution of from about 0.2 to about 0.5% by weight of 3,4-dichlorobenzyl alcohol in combination with about 30% by weight of n-propanol and 40% by weight of isopropanol, to which has been added either or both of benzalkonium chloride in an amount of about 0.2% by weight based on the total aqueous solution, and/or a tertiary phosphoric acid ester of $C_{12}$ to $C_{14}$ fatty alcohol tetraglycol ether.

In addition, the composition can also contain one or more of the previously mentioned auxiliaries such as buffers, perfumes and the like.

The following Examples describe, by way of illustration only, the preparation of microbicidal compositions according to this invention.

EXAMPLE 1

Isopropanol (40 g.) n.-propanol (30 g.), 3,4-dichlorobenzyl alcohol (0.5 g.), the tertiary phosphoric acid dester of $C_{12}/C_{14}$-fatty alcohol tetraglycol ether (1.5 g.), lactic acid (0.05) an aqueous 50% strength (by weight) sodium lactate solution (1.25 g.) and a perfume oil (0.1 g.) are mixed with sufficient demineralized water to yield a 100 g mixture. The components are mixed by stirring or shaking to afford a microbicidal composition suitable for topical administration.

EXAMPLE 2

Isopropanol (40 g.), n-propanol (30 g.), 3,4-dichlorobenzyl alcohol (0.3 g.), benzalkonium chloride (0.2 g.) are mixed with sufficient demineralized water to yield a 100 g. mixture. The components are mixed by stirring or shaking to afford a microbicidal composition suitable for topical application.

EXAMPLE 3

| Ingredient | % Formula A | % Formula B |
|---|---|---|
| Dichlorobenzyl alcohol (approx. 85% 3,4- with the balance 2,3-) | 0.50 | 0.30 |
| n-Propanol | 40.00 | 40.00 |
| Isopropanol | 30.00 | 30.00 |
| Lactic acid | 0.5 | 0.5 |
| 50% Sodium lactate solution | 1.25 | 1.25 |
| III° Phosphoric acid ester of $C_{12}$-$C_{14}$ fatty acid tetraglycol ether | 1.5 | 1.5 |
| Benzalkonium chloride (90% use) | — | 2.22 |
| Demineralized water | qs 100 | qs 100 |

The minimum inhibitory concentrations of these two formulations against a variety of organisms can be seen from Table III:

Table III

| | MIC, % Concentration | | | |
|---|---|---|---|---|
| | Formulation A | | Formulation B | |
| Organism | with serum | without serum | with serum | without serum |
| S. aureus SG 511 | 12.5 | 6.25-12.5 | — | 0.1 |
| E. coli C 165 | — | 6.25 | 6.25 | 6.25 |
| Ps. pyocyaneus V 7602 | 6.25 | 6.25 | 6.25 | 6.25 |
| B. proteus | 6.25 | 6.25 | 6.25 | 6.25 |
| Cand. albicans | 6.25 | 6.25 | 6.25 | 6.25 |
| Myc. smegmatis | 6.25 | 1.56 | 1.56 | 0.2 |
| Mycoplasma MS | — | 5 | — | 2.5 |
| Mycoplasma $S_6$ | — | 1.25 | — | 0.6 |
| Mycoplasma gran. | — | 5 | — | 1.25 |

What is claimed is:

1. A microbicidal composition consisting of an aqueous solution of from 0.1 to 1% by weight of said composition of at least one dichlorobenzyl alcohol selected from the group consisting of 2,3-dichlorobenzyl alcohol, 2,4-dichlorobenzyl alcohol, 3,4-dichlorobenzyl alcohol and 2,6-dichlorobenzyl alcohol in combination with from 65 to 75% by weight of said composition of at least one propanol selected from the group consisting of n-propanol and isopropanol.

2. A microbicidal composition according to claim 1 wherein said 65 to 75% propanol consists of a mixture of n-propanol and isopropanol.

3. A microbicidal composition according to claim 2 wherein the ratio of n-propanol to isopropanol is 3:4.

4. A microbicidal composition according to claim 1 wherein said dichlorobenzyl alcohols include at least 3,4-dichlorobenzyl alcohol.

5. A microbicidal composition according to claim 1 consisting of an aqueous solution of from about 0.2 to about 0.5% by weight of said aqueous solution of 3,4-dichlorobenzyl alcohol in combination with about 30% by weight of said aqueous solution of n-propanol and about 40% by weight of said aqueous solution of isopropanol.

6. A topical antimicrobial formulation for application to the skin of humans and animals, at least 95% of said formulation consisting of an aqueous microbicidal composition according to claim 1, the balance of said formulation comprising at least one topical auxiliary selected from the group consisting of an antibacterial quaternary ammonium salt, a tris-(fatty alcohol tetraglycol ether)

ester of orthophosphoric acid wherein the fatty alcohol has 12 to 14 carbon atoms, and a buffering agent.

7. A topical antimicrobial formulation according to claim 6 wherein at least 95% of said formulation consists of an aqueous solution of from about 0.2 to about 0.5% by weight of said aqueous solution of 3,4-dichlorobenzyl alcohol in combination with about 30% by weight of said aqueous solution of n-propanol and 40% by weight of said aqueous solution of isopropanol, said formulation further containing about 0.2% by weight based on said aqueous solution of benzalkonium chloride.

8. A topical antimicrobial formulation according to claim 6 wherein at least 95% of said formulation consists of an aqueous solution of from about 0.2 to about 0.5% by weight of said aqueous solution of 3,4-dichlorobenzyl alcohol in combination with about 30% by weight of said aqueous solution of n-propanol and 40% by weight of said aqueous solution of isopropanol, said formulation further containing about 2% by weight based on said aqueous solution of a tris-(fatty alcohol tetraglycol ether)ester of orthophosphoric acid wherein the fatty alcohol has 12 to 14 carbon atoms.

9. A microbicidal composition consisting of an aqueous solution of about 0.3% by weight of said aqueous solution of 3,4-dichlorobenzyl alcohol, about 30% by weight of said aqueous solution of n-propanol and 40% by weight of said aqueous solution of isopropanol.

10. A topical antimicrobial formulation for application to the skin of humans and animals, at least 95% of said formulation consisting of the aqueous solution according to claim 9, the balance of said composition comprising about 0.2% by weight of said aqueous solution of benzalkonium chloride.

11. A topical antimicrobial formulation for application to the skin of humans and animals, at least 95% of said formulation consisting of the aqueous solution according to claim 9, the balance of said formulation comprising about 2% by weight based on said aqueous solution of a tris-(fatty alcohol tetraglycol ether)ester of orthophosphoric acid wherein the fatty alcohol has 12 to 14 carbon atoms.

12. The method of disinfecting the skin of humans or animals which consists of topically applying to said skin a microbicidally effective quantity of a topical formulation in which at least 95% of said formulation consists of an aqueous solution of from 0.1 to 1% by weight of said aqueous solution of at least one dichlorobenzyl alcohol selected from the group consisting of 2,3-dichlorobenzyl alcohol, 2,4-dichlorobenzyl alcohol, 3,4-dichlorobenzyl alcohol and 2,6-dichlorobenzyl alcohol in combination with from 65 to 75% by weight of said aqueous solution of at least one propanol selected from the group consisting of n-propanol and isopropanol.

13. The method according to claim 12 wherein at least 95% of said formulation consists of an aqueous solution of from about 0.2 to about 0.5% by weight of said aqueous solution of 3,4-dichlorobenzyl alcohol in combination with about 30% by weight of said aqueous solution of n-propanol and 40% by weight of said aqueous solution of isopropanol, the balance of said formulation comprising about 0.2% by weight based on said aqueous solution of benzalkonium chloride.

14. The method according to claim 12 wherein at least 95% of said formulation consists of an aqueous solution of from about 0.2 to about 0.5% by weight of said aqueous solution of 3,4-dichlorobenzyl alcohol in combination with about 30% by weight of said aqueous solution of n-propanol and 40% by weight of said aqueous solution of isopropanol, the balance of said formulation comprising about 2% by weight based on said aqueous solution of a tris-(fatty alcohol tetraglycol ether)ester of orthophosphoric acid wherein the fatty alcohol has 12 to 14 carbon atoms.

15. The method according to claim 12 wherein at least 95% of said formulation consists of an aqueous solution consisting of about 0.3% by weight of said aqueous solution of 3,4-dichlorobenzyl alcohol, about 0% by weight of said aqueous solution of n-propanol and about 40% by weight of said aqueous solution of isopropanol, the balance of said formulation comprising about 0.2% by weight based on said aqueous solution of benzalkonium chloride.

16. The method according to claim 12 wherein at least 95% of said formulation consists of an aqueous solution consisting of about 0.3% by weight of said aqueous solution of 3,4-dichlorobenzyl alcohol, about 30% by weight of said aqueous solution of n-propanol and about 40% by weight of said aqueous solution of isopropanol, the balance of said formulation comprising 2% by weight based on said aqueous solution of a tris-(fatty alcohol tetraglycol ether)ester of orthophosphoric acid wherein the fatty alcohol has 12 to 14 carbon atoms.

* * * * *